US011642453B2

(12) United States Patent
Makin et al.

(10) Patent No.: US 11,642,453 B2
(45) Date of Patent: May 9, 2023

(54) FLUID INFUSION SYSTEM

(71) Applicant: A.T. STILL UNIVERSITY, Kirksville, MO (US)

(72) Inventors: Inder Raj S. Makin, Mesa, AZ (US); Harry Jabs, Oakland, CA (US); Shervin Tony Hashemian, Scottsdale, AZ (US)

(73) Assignee: A.T. STILL UNIVERSITY, Kirksville, MO (US)

( * ) Notice: Subject to any disclaimer, the term of this patent is extended or adjusted under 35 U.S.C. 154(b) by 384 days.

(21) Appl. No.: 16/060,629

(22) PCT Filed: Jan. 10, 2018

(86) PCT No.: PCT/US2018/013098
§ 371 (c)(1),
(2) Date: Jun. 8, 2018

(87) PCT Pub. No.: WO2018/132430
PCT Pub. Date: Jul. 19, 2018

(65) Prior Publication Data
US 2021/0162118 A1 Jun. 3, 2021

Related U.S. Application Data

(60) Provisional application No. 62/444,657, filed on Jan. 10, 2017.

(51) Int. Cl.
*A61M 5/14* (2006.01)
*A61M 5/142* (2006.01)
(Continued)

(52) U.S. Cl.
CPC ...... *A61M 5/14248* (2013.01); *A61M 5/1408* (2013.01); *A61M 5/14228* (2013.01);
(Continued)

(58) Field of Classification Search
CPC .......... A61M 5/14248; A61M 5/14244; A61M 2005/14268; A61M 5/142; A61M 37/0015; A61M 2037/0023
See application file for complete search history.

(56) References Cited

U.S. PATENT DOCUMENTS 6,589,229 B1   7/2003  Connelly et al.
7,303,543 B1  12/2007  Maule et al.
(Continued)

FOREIGN PATENT DOCUMENTS

WO   WO-2014132240 A1 *  9/2014  ............. A61M 5/42

OTHER PUBLICATIONS

International Search Report and Written Opinion issued in corresponding International Application No. PCT/US2018/013098, dated Apr. 4, 2018, 10 pages.

*Primary Examiner* — Nathan R Price
*Assistant Examiner* — Courtney B Fredrickson
(74) *Attorney, Agent, or Firm* — Quarles & Brady LLP

(57) ABSTRACT

An infusion system for subcutaneous delivery of a fluid to a subject is disclosed. The infusion system comprises a source of a fluid; a fluid delivery system; a first fluid conduit in fluid communication with the source of the fluid and the fluid delivery system; a fluid injection device configured to be inserted into the skin of a subject for delivering the fluid to the subject; a second fluid conduit in fluid communication with the fluid delivery system and the fluid injection device; and a support frame attached to the source of the fluid and the fluid delivery system, wherein the support frame is configured to mount the source of the fluid and the fluid delivery system on a region of a head of the subject. The fluid delivery system moves the fluid from the source of the fluid, through the first fluid conduit, through the second fluid conduit, and through the fluid injection device.

28 Claims, 13 Drawing Sheets

(51) Int. Cl.
*A61M 37/00* (2006.01)
*A61M 39/24* (2006.01)

(52) U.S. Cl.
CPC .... *A61M 5/14236* (2013.01); *A61M 37/0015* (2013.01); *A61M 39/24* (2013.01); *A61M 2037/0023* (2013.01); *A61M 2205/0294* (2013.01); *A61M 2205/502* (2013.01); *A61M 2205/52* (2013.01); *A61M 2205/8206* (2013.01); *A61M 2250/00* (2013.01)

(56) References Cited

U.S. PATENT DOCUMENTS

| | | | |
|---|---|---|---|
| 7,569,050 B2 | 8/2009 | Moberg et al. | |
| 7,879,025 B2 | 2/2011 | Jacobson et al. | |
| 9,522,263 B2 | 12/2016 | Ross | |
| 2002/0040208 A1* | 4/2002 | Flaherty | A61M 5/14248 604/288.01 |
| 2003/0045837 A1 | 3/2003 | Delmore et al. | |
| 2003/0125661 A1 | 7/2003 | Yerushalmy | |
| 2003/0229336 A1* | 12/2003 | Jacobsen | A61M 5/145 604/890.1 |
| 2006/0264888 A1 | 11/2006 | Moberg et al. | |
| 2006/0264897 A1* | 11/2006 | Lobl | A61P 27/16 604/506 |
| 2008/0097324 A1* | 4/2008 | Adams | A61M 5/14248 604/153 |
| 2008/0255516 A1* | 10/2008 | Yodfat | A61M 5/14248 604/151 |
| 2008/0294109 A1* | 11/2008 | Estes | A61M 5/14244 604/141 |
| 2009/0292329 A1 | 11/2009 | Gibson | |
| 2009/0297372 A1 | 12/2009 | Amirouche et al. | |
| 2010/0049164 A1* | 2/2010 | Estes | A61M 5/1723 604/504 |
| 2011/0054285 A1* | 3/2011 | Searle | A61M 5/16804 600/365 |
| 2011/0213335 A1 | 9/2011 | Burton et al. | |
| 2012/0078216 A1 | 3/2012 | Smith et al. | |
| 2012/0308409 A1 | 12/2012 | Levine | |
| 2013/0178826 A1* | 7/2013 | Li | A61M 5/155 604/506 |
| 2014/0076336 A1* | 3/2014 | Clayton | A61M 31/00 128/865 |
| 2014/0323907 A1 | 10/2014 | Frazier et al. | |
| 2015/0157788 A1* | 6/2015 | Gescheit | A61M 5/14248 604/67 |
| 2015/0169857 A1* | 6/2015 | Wang | A61M 5/14244 604/67 |
| 2015/0190588 A1 | 7/2015 | Hanson et al. | |
| 2016/0184852 A1* | 6/2016 | Fontana | A61M 5/16854 222/1 |

\* cited by examiner

FLUID INFUSION SYSTEM

CROSS-REFERENCE TO RELATED APPLICATIONS

This application represents the U.S. National Stage of International Application No. PCT/US2018/013098, filed Jan. 10, 2018 which claims priority to U.S. Provisional Patent Application No. 62/444,657 entitled "Fluid Infusion System" filed Jan. 10, 2017, which is hereby incorporated by reference in its entirety.

STATEMENT REGARDING FEDERALLY SPONSORED RESEARCH

Not Applicable.

BACKGROUND OF THE INVENTION

1. Field of the Disclosure

This disclosure relates to an infusion system for subcutaneous delivery of a fluid to a subject.

2. Description of the Related Art

Infusion systems can be used for delivering a medication or other fluid to a patient. Infusion systems typically include a cannula that provides a transcutaneous passageway to administer the medication or other fluid to a subcutaneous site on a patient. The cannula is attached to a fluid delivery system. The fluid delivery system is generally placed in fluid communication with the cannula by way of a length of infusion tubing. Infusion sets can be adapted to rest on the skin of the patient, and the cannula may remain in the patient's skin for several days. Infusion systems can be very convenient to a patient, in that accurate doses of medication may be calculated and delivered automatically to a patient at any time during the day or night.

Pump type delivery devices have become an important aspect of modern medical treatments of various types of medical conditions. As pump technologies improve and doctors and patients become more familiar with such devices, the popularity of external medical infusion pump treatment increases and is expected to increase substantially over the next decade. However, many types of pump type delivery devices have been relatively expensive to obtain and to operate over a period of time. Also, stable medication flow rates may be difficult to achieve.

Accordingly, a need exists for improved infusion systems that meet the increased demand for ambulatory infusion devices.

SUMMARY OF THE INVENTION

The present disclosure provides an infusion system for subcutaneous delivery of a fluid to a subject. The infusion system comprises a source of a fluid; a fluid delivery system; a first fluid conduit in fluid communication with the source of the fluid and the fluid delivery system; a fluid injection device configured to be inserted into the skin of a subject for delivering the fluid to the subject; a second fluid conduit in fluid communication with the fluid delivery system and the fluid injection device; and a support frame attached to the source of the fluid and the fluid delivery system, wherein the support frame is configured to mount the source of the fluid and the fluid delivery system on a region of a head of the subject. The fluid delivery system moves the fluid from the source of the fluid, through the first fluid conduit, through the second fluid conduit, and through the fluid injection device. A "subject" is an animal, or a human.

In some embodiments, the fluid delivery system may be configured such that the fluid injection device delivers 10 to 100 microliters per minute of the fluid to the subject. The fluid delivery system may include a pump in fluid communication with the first fluid conduit and the second fluid conduit, the pump moving the fluid from the source of the fluid, through the first fluid conduit, through the second fluid conduit, and through the fluid injection device.

In some embodiments, the pump may be a piezoelectrically actuated pump, a membrane pump, a vane pump, a syringe pump, a peristaltic pump, a scroll pump, a screw pump, a progressing cavity pump, a gear pump, or any other pump-like active or passive fluid delivery system. The pump can comprise one or more double acting piezo actuators. The pump can be valve-less. The pump may produce a pressure of 10 kPa or greater or 100 kPa or greater. The fluid delivery system may include a check valve that prevents backflow into the pump. The fluid delivery system may include a battery power supply in electrical communication with a controller, the controller may be in electrical communication with the battery power supply and the pump, and the controller may be configured to actuate the pump to move the fluid from the source of the fluid, through the first fluid conduit, through the second fluid conduit, and through the fluid injection device. The controller may have a wired communication port to a computer, a smart phone, or appropriate controller module, running software applications with graphical user interfaces for control, monitoring and data logging. The communication may be wireless using a secure wireless communication protocol such as IEEE 802.11 a/b/g/n using encryption for security and safety.

In some embodiments, the fluid injection device comprises: (i) a cannula configured to be inserted into the skin of the subject for delivering the fluid to the subject, and (ii) an adhesive patch system for securing the cannula to the skin of the subject.

In some embodiments, the fluid injection device comprises: (i) a microneedle array including microneedles configured to be inserted into the skin of the subject for delivering the fluid to the subject, and (ii) an adhesive patch system for securing the microneedle array to the skin of the subject.

In some embodiments, the support frame is structured to loop around at least a portion of an ear of the subject. In still other embodiments, the support frame is structured to loop around a neck of the subject. In still other embodiments, the support frame is structured to loop around the top of the head of the subject. In still other embodiments, the support frame is structured to loop around the top and the neck and/or the forehead of the head of the subject. The fluid may comprise a pain medication, or a medication for treating temporomandibular joint pain.

The present disclosure also provides a method for treating temporomandibular joint dysfunction in a subject. The method includes the steps of: (a) providing the infusion system described above; (b) inserting the fluid injection device of the infusion system into the skin of a subject for delivering the fluid to the subject; and (c) activating the fluid delivery system to move the fluid from the source of the fluid, through the first fluid conduit, through the second fluid conduit, and through the fluid injection device, wherein the fluid comprises a medication for treating temporomandibular joint pain. The fluid injection device may be configured programmable such that the flow rate may be changed according to an optimized medication delivery regime.

The present disclosure also provides an infusion system for subcutaneous delivery of a fluid-based medication to a subject. The infusion system comprises: a syringe pump including a reservoir containing a fluid; a fluid conduit in fluid communication with the reservoir; a fluid injection device configured to be inserted into the skin of a subject for delivering the fluid to the subject, the fluid injection device being in fluid communication with the fluid conduit; and a support frame attached to the syringe pump, wherein the support frame is configured to mount the syringe pump on a region of a head of the subject. In still other embodiments, the support frame is structured to loop around the top of the head of the subject. In still other embodiments, the support frame is structured to loop around the top and the neck and/or the forehead of the head of the subject. The syringe pump moves the fluid from the reservoir, through the fluid conduit, and through the fluid injection device.

In some embodiments, the syringe pump comprises a plunger that translates in the reservoir for moving the fluid from the reservoir and into the fluid conduit. The syringe pump may further comprise a draw bar that advances the plunger. The syringe pump may further comprise a linear screw that moves the draw bar. The syringe pump may further comprise a stepper motor that actuates the linear screw.

In some embodiments, the infusion system may further comprise a battery power supply in electrical communication with a controller, the controller is in electrical communication with the battery power supply and the stepper motor, and the controller is configured to actuate a stepper motor to move the fluid from the reservoir, through the fluid conduit, and through the fluid injection device.

In some embodiments, the fluid injection device may comprise: (i) a cannula configured to be inserted into the skin of the subject for delivering the fluid to the subject, and (ii) an adhesive patch for securing the cannula to the skin of the subject.

In some embodiments, the fluid injection device comprises: (i) a microneedle array including microneedles configured to be inserted into the skin of the subject for delivering the fluid to the subject, and (ii) an adhesive patch system for securing the microneedle array to the skin of the subject.

In some embodiments, the infusion system may comprise a power source, which may be one or more batteries. In some embodiments, battery-operation may be preferred over an AC connection.

The present disclosure also provides a method for treating temporomandibular joint dysfunction in a subject. The method includes the steps of: (a) providing the infusion system described above; (b) inserting the fluid injection device of the infusion system into the skin of a subject for delivering the fluid to the subject; and (c) activating the syringe pump to move the fluid from the reservoir, through the fluid conduit, and through the fluid injection device, wherein the fluid comprises a medication for treating temporomandibular joint pain.

It is therefore an advantage of the disclosure to provide a microfluidic infusion approach for continuous drug delivery.

It is another advantage of the disclosure to provide a microfluidic infusion approach for continuous drug delivery for temporomandibular joint (TMJ) dysfunction treatment and other oral applications.

It is another advantage of the disclosure to provide an infusion system having continuous on-demand operation.

It is another advantage of the disclosure to provide an infusion system having continuous on-demand operation programmed according to an optimized medication delivery regime.

It is another advantage of the disclosure to provide an infusion system that is easy to wear (ergonomic).

It is another advantage of the disclosure to provide an infusion system that is securely but comfortably attached to the head (ergonomic).

It is another advantage of the disclosure to provide an infusion system that is miniaturized.

It is another advantage of the disclosure to provide an infusion system that has a flow rate of fluid of 10 to 100 microliters per minute (µl/min), preferably at least 83 µl/min (5 milliliters per hour).

It is another advantage of the disclosure to provide an infusion system that has positive pressure.

It is another advantage of the disclosure to provide an infusion system that has no back flow of fluid.

These and other features, aspects, and advantages of the present disclosure will become better understood upon consideration of the following detailed description, drawings and appended claims.

DETAILED DESCRIPTION OF THE INVENTION

The present disclosure provides an infusion system for subcutaneous delivery of a fluid to a subject. The infusion system may generally comprise a source of a fluid; a fluid delivery system; a first fluid conduit in fluid communication with the source of the fluid and the fluid delivery system; a fluid injection device configured to be inserted into the skin of a subject for delivering the fluid to the subject; a second fluid conduit in fluid communication with the fluid delivery system and the fluid injection device; and a support frame attached to the source of the fluid and the fluid delivery system, wherein the support frame is configured to mount the source of the fluid and the fluid delivery system on a region of a head of the subject. The fluid delivery system moves the fluid from the source of the fluid, through the first fluid conduit, through the second fluid conduit, and through the fluid injection device.

Figure 1:
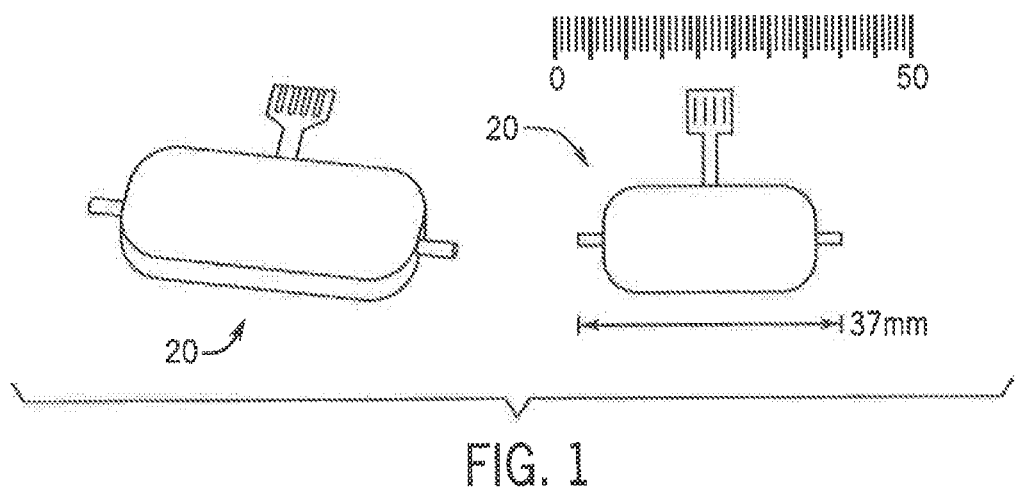
FIG. 1 is a depiction of a micropump suitable for use in an infusion system according to the disclosure.

A non-limiting example embodiment of the infusion system for use in treating temporomandibular joint (TMJ) pain was developed. This embodiment of the infusion system used a piezoelectric micropump because of its advantageous device parameters for a TMJ prototype. This embodiment of the infusion system reduced the operating voltage inherent with piezoelectric actuators. The piezoelectric micropump 20 used in the infusion system was a Model mp6 manufactured by Bartels Mikrotechnik, GmbH in Germany and a photograph along with a scale drawing is shown in FIG. 1. The micropump 20 measured 30 mm×15 mm×3.8 mm and weighed 2 grams. The micropump 20 is of the self-priming type. The micropump 20 produces a maximum flow rate for water or aqueous solutions of 7,000 µl/min at a pressure of 70 kPa. While the pressure is more than sufficient, the flow rate may preferably be lower but can easily be throttled or baffled.

This embodiment of the infusion system capitalized on the high flow rate capability of the micropump 20 in favor of minimizing its operating voltage, power consumption and operating noise. This can be done in at least two configurations of the infusion system.

In the first configuration, a single micropump 20 is used and a custom-built controller can be developed that optimizes the drive waveform to achieve the lowest operating voltage while providing a maximum flow rate of 83 µl/min at a minimum pressure of 40 kPa.

In the second configuration, two identical micropumps 20 can be used. The micropumps 20 can be stacked back-to-back for the most compact arrangement and plumbed in series. It is assumed that when the operating voltage is reduced that the deflection of the piezoactuator becomes so small that normal operation would cease or become unstable. This effect may be overcome by plumbing two pumps in series, essentially creating a two-stage pump or one pump with two chambers and four valves. It is also conceivable that by optimizing the waveforms to the four piezo actuators and their phase relations the pump performance might be enhanced while the operating voltage might be lowered even further, as will be discussed in further detail below.

Figure 2:
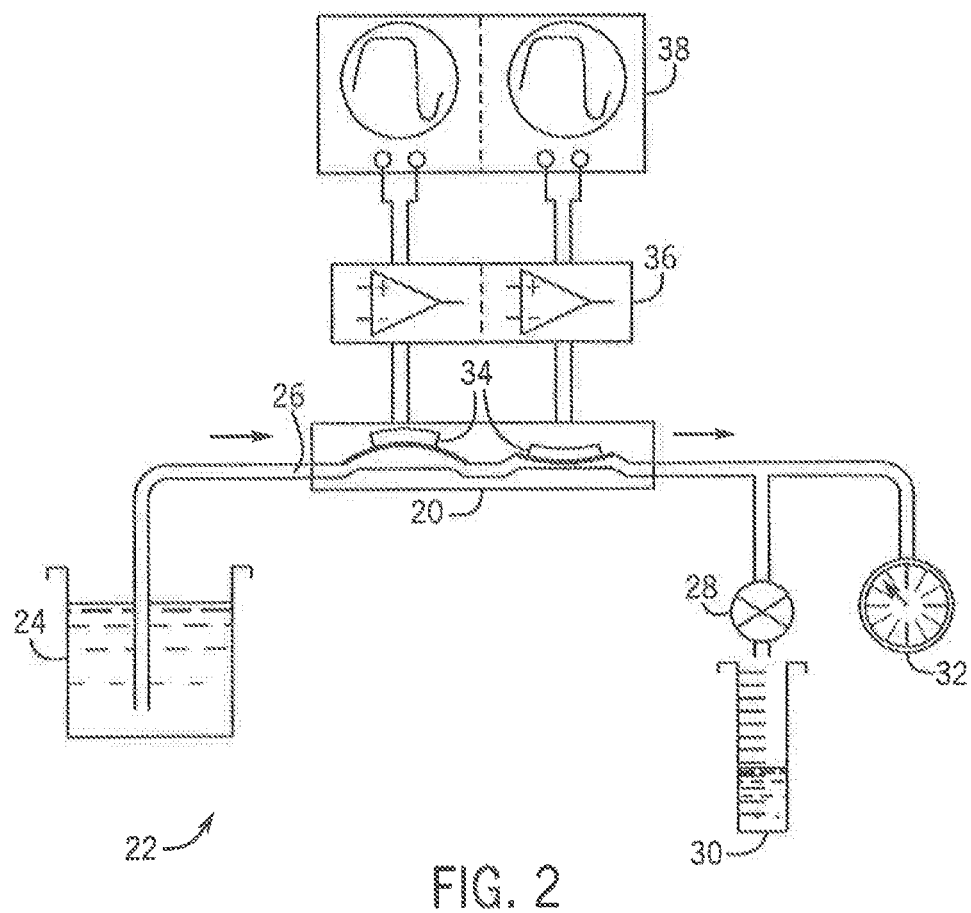
FIG. 2 is a schematic diagram of a bench-top setup for pump controller development in a single-pump configuration suitable for use in an infusion system according to the disclosure.

In the first step of proof of concept, a pump 20, which may be a single Bartels mp6 pump, can be set up in a breadboard system 22 as schematically shown in FIG. 2. The pump will draw from a reservoir 24 at the intake 26 and discharge through an adjustable throttle valve 28 into a collection vessel 30 for flow rate measurement. The throttle valve 28 may be a multi-turn needle valve and can be gradually closed to simulate back pressure to characterize the pump 20. A pressure gauge 32 upstream from the throttle valve in the pump's discharge line measures the pressure produced. Two piezoelectric actuators 34 of the pump 20 can be controlled independently. A two-channel linear amplifier 36 capable of output voltages of at least 150V and a bandwidth of at least 10 kHz to amplify arbitrary waveforms with low distortion can be used to drive the two piezo actuators 34 separately. The linear amplifier 36 is driven by a two-channel arbitrary waveform generator 38 capable of generating two separate arbitrary waveforms. The linear amplifier 36 is beneficial because arbitrary waveform generators typically provide less than 20V output. The linear amplifier 36 may be replaced with a class-D amplifier to increase energy efficiency.

With the single-pump setup thus described, the waveform for both channels of the two-channel arbitrary waveform generator 38 is at first set to sinusoidal to reproduce the manufacturers specifications. If these are met, then the waveforms will be changed independently as will the phase relationship between both channels. Parameter fields of flow rate and produced pressure as functions of waveform, frequency, amplitude, and phase angle can be mapped to determine the optimal drive conditions of the two piezo actuators 34. If drive conditions are optimized, the operating voltage may be minimized while maintaining a minimum flow rate of 83 µl/min at a minimum pressure of 40 kPa. The mapped-out parameter field may be stored in a data base or lookup table and a system controller may reference to this data base or lookup table for optimal pumping characteristics under various operating conditions.

Figure 3:
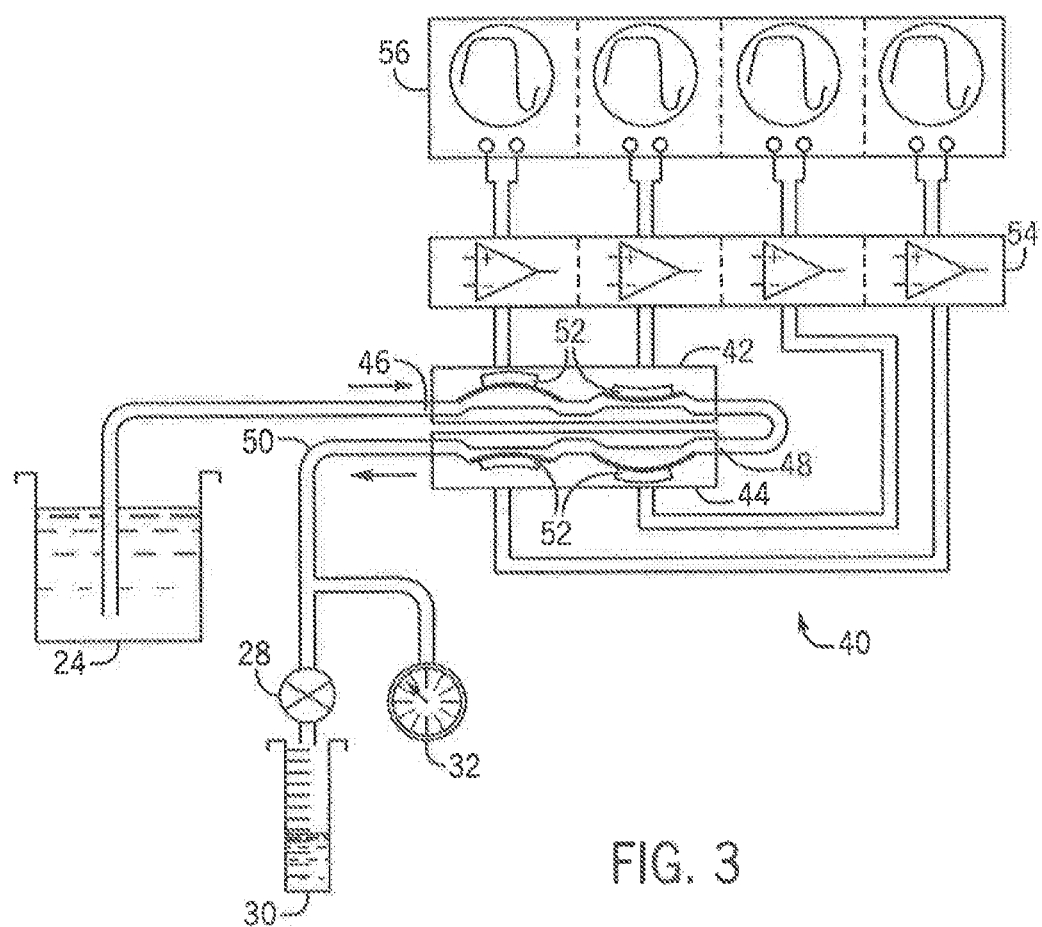
FIG. 3 is a schematic diagram of a bench-top setup for pump controller development in a double-pump configuration (two-stage pump configuration) suitable for use in an infusion system according to the disclosure.

If the setup described in the above paragraph and shown in FIG. 2 does not yield sufficient improvement of operating parameters for a TMJ infusion system, one can further improve these parameters in a two-pump configuration with a breadboard system 40 shown in FIG. 3. The configuration is akin to a two-stage pump system where a first pump 42 and a second pump 44 are plumbed in series as shown in FIG. 3. This configuration improves operating parameters because the total pressure is now divided into two with each pump 42, 44 providing its differential pressure. Both differential pressures are additive.

The first pump 42 will draw from a reservoir at the intake 46 and discharge directly into the intake 48 of the second pump 44. The second pump 44 will discharge through an adjustable throttle valve 28 into a collection vessel 30 for flow rate measurement. The throttle valve 28 may be a multi-turn needle valve that can be gradually closed to simulate back pressure to characterize the first pump 42 and the second pump 44. A pressure gauge 32 upstream from the throttle valve 28 in the second pump's 44 discharge line 50 measures the total pressure produced. The two piezoelectric actuators in each pump can be controlled independently. There is a total of four independently controllable piezoelectric actuators 52 for the two pumps 42, 44. A four-channel linear amplifier 54 capable of output voltages of at least 150V and a bandwidth of at least 10 kHz to amplify arbitrary waveforms with low distortion will be used to drive the four piezo actuators 52 separately. The linear amplifier 54 is driven by a four-channel arbitrary waveform generator 56 capable of generating four separate arbitrary waveforms. The linear amplifier 54 is beneficial because arbitrary waveform generators typically provide less than 20V output. The linear amplifier 54 may be replaced with a class-D amplifier to increase energy efficiency.

With the single-pump setup thus described, the waveform for both channels of the two-channel arbitrary waveform generator 38 is at first set to sinusoidal to reproduce the manufacturers specifications. If these are met, then the waveforms will be changed independently as will the phase relationship between both channels. Parameter fields of flow rate and produced pressure as functions of waveform, frequency, amplitude, and phase angle can be mapped to determine the optimal drive conditions of the two piezo actuators 34. If drive conditions are optimized, the operating voltage may be minimized while maintaining a minimum flow rate of 83 µl/min at a minimum pressure of 40 kPa. The mapped-out parameter field may be stored in a data base or lookup table and a system controller may reference to this data base or lookup table for optimal pumping characteristics under various operating conditions.

With the double-pump setup thus described and schematically shown in FIG. 3, the waveform for both channels is at first set to sinusoidal to reproduce the manufacturers specifications. In the double-pump configuration, the phase relation of the wave forms between the two pumps must be considered to achieve optimal overall performance.

Specifically, the phase relationship between the discharge piezo actuator of the first pump 42 and the intake piezo actuator of the second pump 44 must be optimized to assure unimpeded flow of the incompressible aqueous media. If the manufacturer's specifications are met, then the waveforms will be changed independently as will the phase relationship between all four channels. Parameter fields of total flow rate and total produced pressure as a function of waveform, frequency, amplitude, and phase angle can be mapped to determine the optimal drive conditions of all four piezo actuators 52. It is expected that if drive conditions are optimized the operating voltage of each piezo actuator may be minimized while maintaining a minimum total flow rate of 83 µl/min at a minimum pressure of 40 kPa. The mapped-out parameter field may be stored in a data base or lookup table and a system controller may reference to this data base or lookup table for optimal pumping characteristics under various operating conditions.

Once the optimal waveforms, frequencies and phase relations of the drive signals for the piezoelectric actuator micropumps are established, a microcontroller can be programmed to generate these signals. The microcontroller may access the parameter field data base or lookup table for this purpose. Typically, there will be additional programming to facilitate operator control to affect the operating characteristics of the pump such as a variable flow rate, up or down ramps of flow rate, timed operation, or a combination of these modes.

Figure 4:
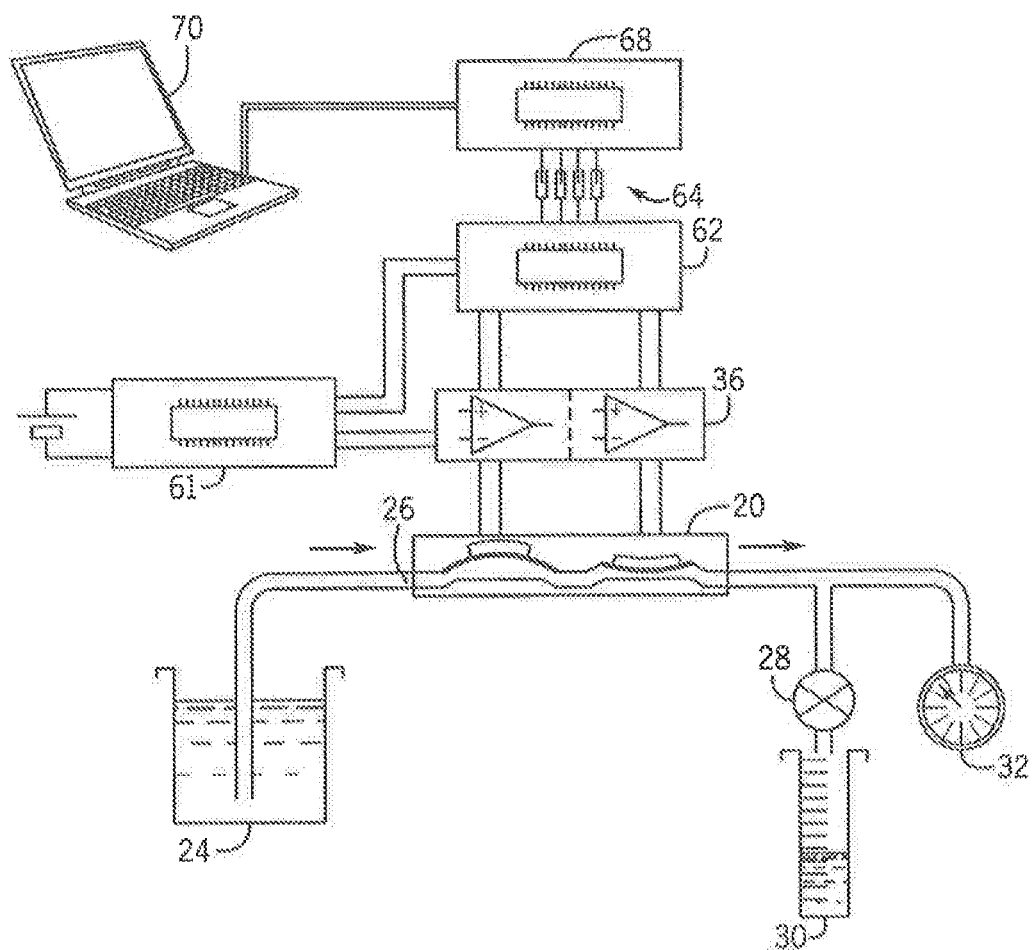
FIG. 4 is a schematic diagram of a bench-top setup for microcontroller programming. The single-pump configuration is shown but the double-pump configuration is analogous, except that four channels are required to drive four piezo actuators.

The programming of a microcontroller typically requires a number of firmware builds and tests of proper operation. Therefore, the microcontroller programming step is designed as bench-top setup with a PC computer as schematically shown in FIG. 4. The hardware that will become part of an actual TMJ infusion system is already selected to meet the space and power requirements and are designed to operate off of the actual battery type to be used in the TMJ prototype infusion system, in a non-limiting example a rechargeable Li-Ion CR2032 button cell with 3.7V nominal voltage may be used. As microcontroller 62, the MSP430 family of microcontrollers manufactured by Texas Instruments are non-limiting examples of suitable devices. They are specifically designed for portable applications with minimal power draw and several low-power and ultra-low power sleep modes to maximize battery life. For the TMJ prototype infusion system, the MSP430F1611 is beneficial because it is a 16-bit high-performance microcontroller that has a non-volatile flash memory, 12-bit A/D and D/A converters 61, four sleep modes and a JTAG in-circuit programming port. A micro connector 64 (e.g. JTAG in-circuit programming) connects the microcontroller 62 to a programmer 68 that is connected to a PC computer 70. There are several integrated development environments (IDEs) available to program the firmware, compile, link and upload the executable file to the microcontroller's memory and run debugging sessions. When firmware programming is complete, the JTAG connection is removed and the system is running for as long as battery power is provided.

Generally, piezo actuation may be performed at approximately 100 Hz to achieve optimal flow rate and head pressure. At this frequency, the flow rate was approximately 300 ml/h. However, the target flow rate for the prototype was specified to 5 ml/h. The flow rate could be reduced to 72 ml/h by reducing the piezo actuator frequency to 23 Hz, the minimal frequency the pump would operate properly. To reduce the flow rate to 5 ml/h, a throttle was installed at the discharge port.

Figure 5:
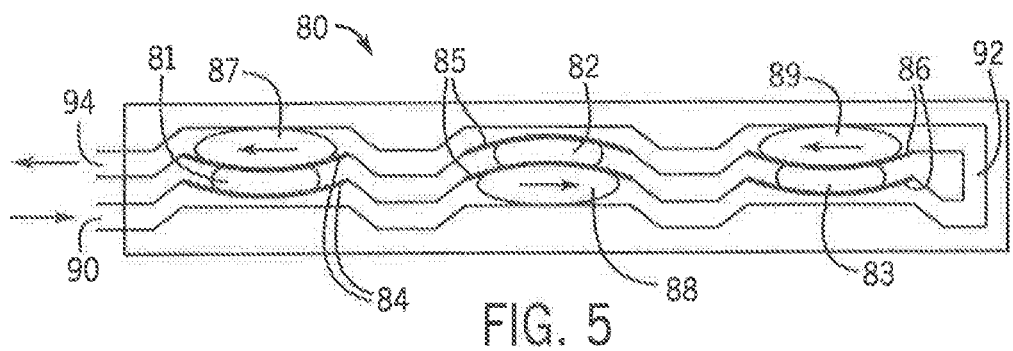
FIG. 5 is a schematic diagram of a micropump configuration suitable for use in an infusion system according to the disclosure.

FIG. 5 shows an improved pump disclosed to solve insufficiencies of commercially available pumps. A pump 80 is disclosed, which may be a modified piezo pump. In this embodiment, the pump 80 uses three piezo actuators 81, 82, 83 of suitable dimensions. Every piezo actuator 81, 82, 83 has a diaphragm 84, 85, 86 bonded to each side. Each diaphragm 84, 85, 86 operates one pump chamber 87, 88, 89 (not shown each opposing chamber for chambers 87, 88, 89) for a total of six pump chambers altogether. When the piezo actuators 81, 82, 83 are energized with suitable waveforms and suitable timing and phase relationship with respect to each other, then the first three pump chambers (including chamber 88) can draw fluid into the intake port 90 and discharge into the return loop 92. The return loop 92 may generally feed the fluid back to the three piezo actuators 81, 82, 83 on the discharge side 94. The pump arrangement generally operates as a series of six piezo actuators, including 81, 82, 83, performing a peristaltic-like movement to pump fluid. However, by feeding the fluid back to the actuators 81, 82, 83 on the discharge side 94, each piezo actuator 81, 82, 83 is double-acting, i.e., drawing fluid into the chamber on the intake side 90 while pushing fluid out of the chamber on the discharge side 94.

The pump 80 may be generally designed as valve-less (i.e., the piezo actuators 81, 82, 83 can selectively open and close with the selective actuation of each respective diaphragm 84, 85, 86). One non-limiting advantage of the valve-less construction of the pump 80 is that it will remain clean (i.e. there will be no "sticky" valves) if the pump was not dried properly after fluid use. The double-acting piezo actuators 84, 85, 86 allow the number of pump chambers 87, 88, 89 to be doubled for a given number of piezo actuators 84, 85, 86 and thereby improved pumping efficiency is achieved. Furthermore, the actuator frequency can now be greatly reduced along with the effective pump volume per stroke of the actuator or actuators. A preferred pump rate of 5 ml/h for drug delivery is achieved with proper sizing and control of the diaphragm size and chamber volumes. The system is further simplified because a throttle may no longer be required, which results in space and energy savings.

Figure 6:
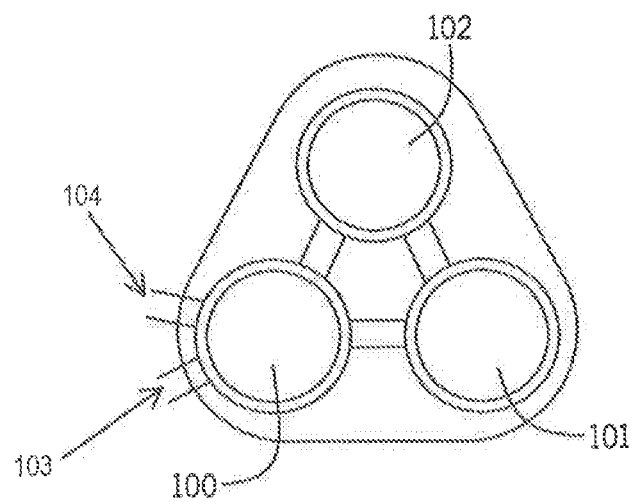
FIG. 6 is another schematic diagram of a micropump configuration suitable for use in an infusion system according to the disclosure.

FIG. 6 shows three actuators 100, 101, 102 can be arranged in a triangular pattern, increasing the physical size of the pump only marginally over a two-chamber commercial pump, but offering a three-fold increase in the number of pump chambers. A compact arrangement in triangular configuration is shown in FIG. 6 arranging the three actuators 100, 101, 102 between an intake 103 and a discharge 104. It is to be appreciated that there can be any number of actuators that can be arranged as double-acting piezo actuators. Generally, increasing the number of actuators increases the efficiency of the pumping process and also lowers the achievable pump rate. To achieve the highest degree of compactness, the actuators 100, 101, 102 can be arranged in a circular pattern and may be stacked upon each other to produce a different aspect ratio of width by length versus height.

Figure 9:
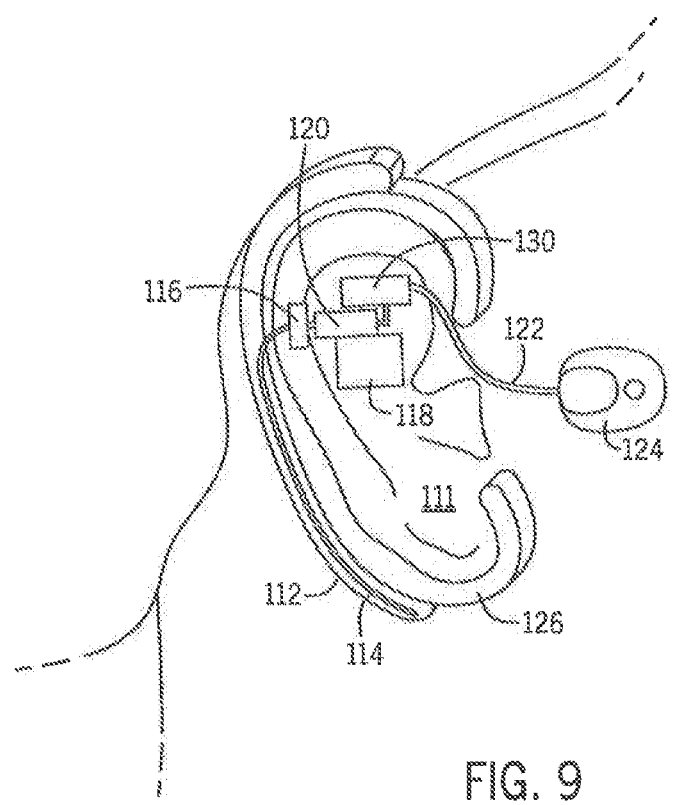
FIG. 9 is a schematic rendition of another TMJ prototype infusion system according to the disclosure worn by a human subject.

With the optimal operating parameters determined, the single-pump configuration (FIGS. 2 and 4), double-pump configuration (FIG. 3), pump 80 shown in FIG. 5, or a configuration according to the designs discussed in reference to FIG. 6 can be selected and the microcontroller programmed and the hardware for the TMJ prototype infusion system can be assembled. To achieve the highest degree of compactness, ruggedness and serviceability it is advantageous if the pump(s), battery and electronics be mounted to a single glass-epoxy printed circuit board. This board will then be mounted to a well-fitting ear hook as schematically shown in FIG. 9. To further increase compactness and shortening of interconnections the printed circuit board may be populated with components on both sides.

This embodiment of the infusion system depicted in FIG. 9 is based on components available from manufacturers and vendors. Table 1 is a compilation of components suitable for use in this embodiment of the infusion system. It is to be appreciated that these components are non-limiting examples of components that could be used in this system. At least one example of components that could be used instead of those listed in the table are the micropumps disclosed in FIGS. 5 and 6, which may be implemented in any of the embodiments discussed herein.

Figure 7:
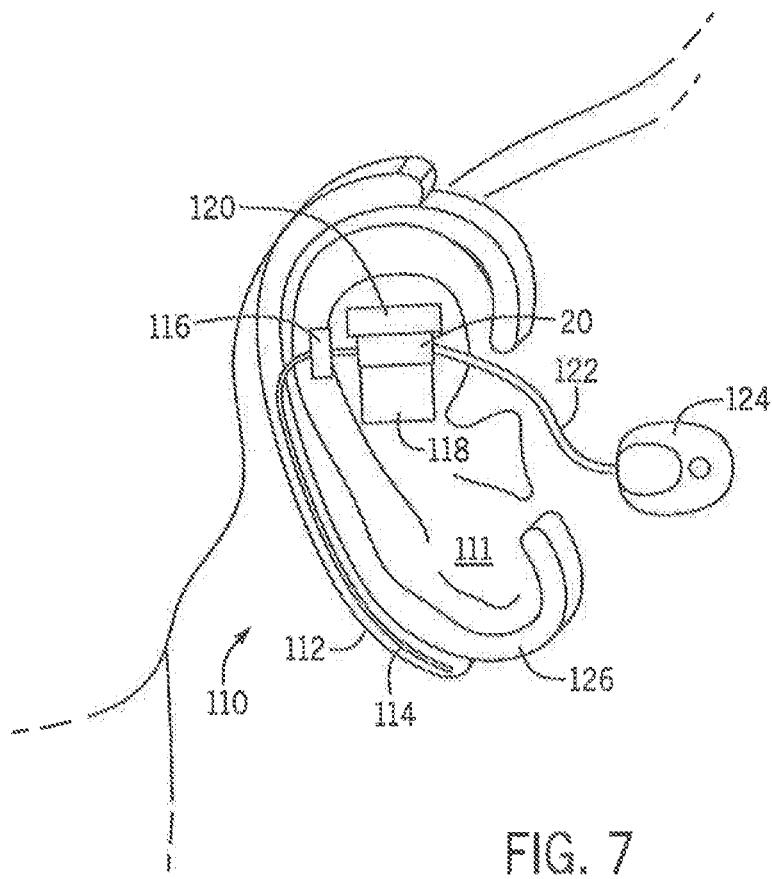
FIG. 7 is a schematic rendition of a TMJ prototype infusion system according to the disclosure worn by a human subject.

As shown in FIG. 7, a non-limiting example embodiment of the infusion system 110 for use in treating temporomandibular joint (TMJ) pain was developed. The infusion system 110 is positioned to be worn on or around the ear 111 of a subject. The infusion system 110 generally comprises a disposable reservoir 112 having a siphon tube 114 positioned therein, the distal end of the siphon tube 114 being connected with a septum port 116. The septum port 116 is connected with the micropump 20. The micropump 20 can be connected to a power source 118, which in some instances can be a battery sufficient to power the infusion system 110, and a controller board 120 configured to control the operation of the micropump 20 and the infusion system 110. The micropump 20 is connected to a patch 124 via a conduit 122 configured to provide fluid communication between the micropump 20 and the patch 124. In some embodiments, the patch 124 can be a diabetic cannula patch. The infusion system 110 can be supported around the ear 111 of a subject by a support frame 126, in some instances an ear hook, that wraps around the ear 111 of the subject to provide structural support to the infusion system 110.

Another non-limiting example embodiment of the infusion system for use in treating temporomandibular joint (TMJ) pain was developed. The miniaturization of pumps has naturally led to micromachined or MEMS pumps (Micro-Electro-Mechanical System). Micromachining is a process that originated from the semiconductor industry processing silicon wafers. There are two distinct kinds of micromachining processes. Surface micromachining uses a succession of thin film deposition and selective etching, whereas bulk micromachining defines 3-dimensional structures by selectively etching inside the wafer substrate.

There are some manufactures who fabricate micromachined pumps for special applications to a select target group. One such pump is presented herein in the second configuration for a TMJ prototype infusion system.

Debiotech S. A., a Swiss company located in Lausanne, Switzerland, has developed a micromachined pump 130. It must be noted that this pump is piezo-actuated, like the Bartels mp6 pump, and will therefore require substantial

TABLE 1

List of components.

Figure 8:
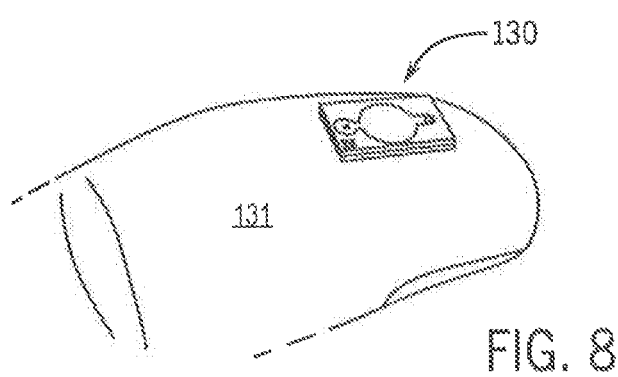
FIG. 8 is a nanopump suitable for use in an infusion system according to the disclosure.

| Item | Description | Source |
|---|---|---|
| Pump(s) Qty.: 1-2 | Piezoelectric micropump Model: mp6 | Bartels Mikrotechnik GmbH |
| Signal generator Qty.: 2-4 | Arbitrary wave generator, Model: DDS-3x25 | Mfg.: Hantek |
| Linear amplifier | High-voltage linear amplifier | Custom design with high-voltage MOSFETs or bipolar transistors. |
| Pressure gauge | Silicon pressure sensor, Model: SSCSANN001BGAA5 | Mfg.: Honeywell |
| Programmer | Emulator/simulator MSP430 USB programming and debugging interface Model.: MSP-FET430UIF | Mfg.: Texas Instruments |
| Microcontroller | Part#: MSP430F1611 | Mfg.: Texas Instruments |
| DC-DC converter | Convert battery voltage to approximately 150 VDC for linear amplifier | Custom design with switched inductor and high-voltage MOSFETs |
| Ear hook | Earhook looping entirely around auricle for excellent hold. Model: 56518 | Mfg.: Motorola |
| Programming software | Integrated development environment software suite. Model: Code Composer Studio, Version 5.3.0 | Mfg.: Texas Instruments | operating voltage in excess of 100V with the possibility to minimize this voltage in an optimization process similar to the one described above. Still, this pump 130 is used as a design concept here because the pump is significantly smaller in size, has a much lower flow rate and presumably a much lower power consumption. FIG. 8 depicts the small size of the pump in reference to the size of a typical human finger 131. The Nanopump™ pump is engineered to be self-priming and immune to gas bubbles. It has sufficient pressure capability to overcome the blood pressure. The manufacturer does not specify the maximum flow rate but quotes a volume of 0.2 µl per stroke. Assuming that the pump is capable of 100 strokes per second, the maximum flow rate is estimated at 120 µl/min presumably in free-flow with no back pressure.

In this embodiment of the infusion system shown in FIG. 9, the Bartels mp6 pump is replaced by the Debiotech Nanopump™ 110 pump while all other major components remain the same as in FIG. 7. However, the driver hardware must be modified to match the Nanopump™ pump. A prototype worn by a subject is schematically shown in FIG. 9. Advantages gained from using the Debiotech Nanopump™ pump instead of the Bartels mp6 pump are smaller component size, less weight, and due to lower energy consumption, a smaller battery, or a longer battery life or a combination thereof.

Figure 10A:
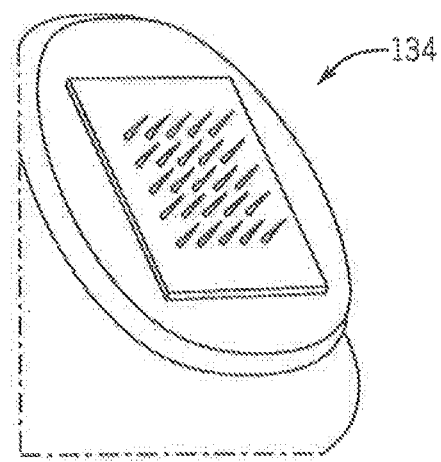
FIGS. 10A and 10B show a microneedle array suitable for use in an infusion system according to the disclosure.
Figure 10B:
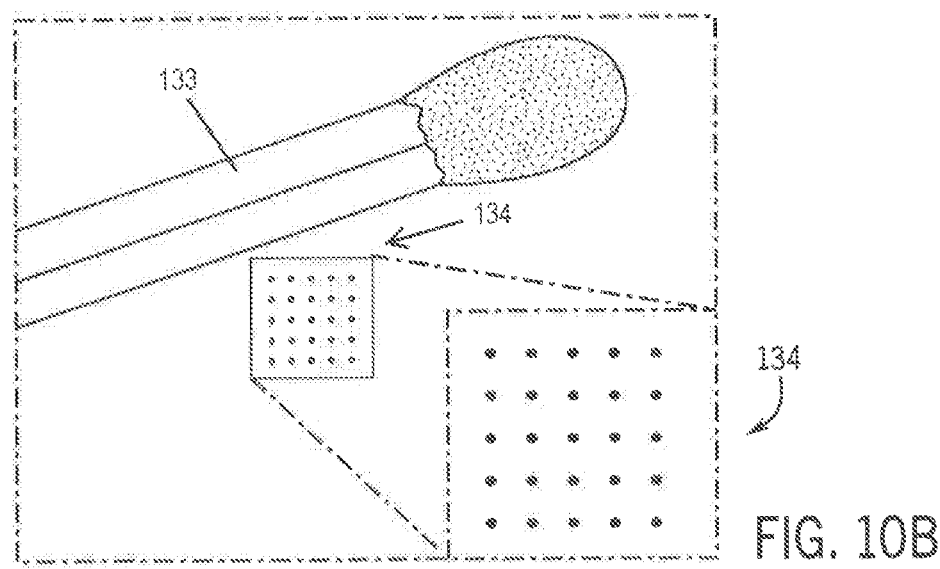
Figure 11:
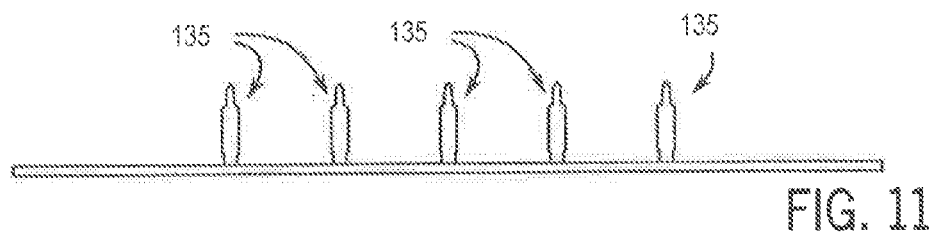
FIG. 11 is a side view of the microneedle array of FIG. 10.
Figure 12A:
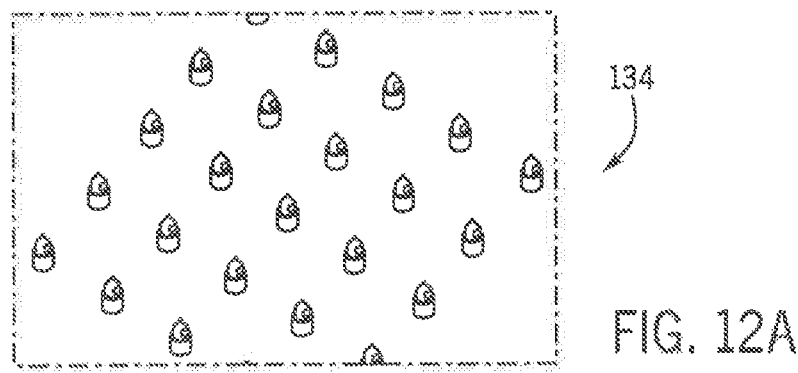
FIGS. 12A, 12B, 12C, and 12D micrograph-scale drawings detailing a microneedle array suitable for use in an infusion system according to the disclosure.
Figure 12B:
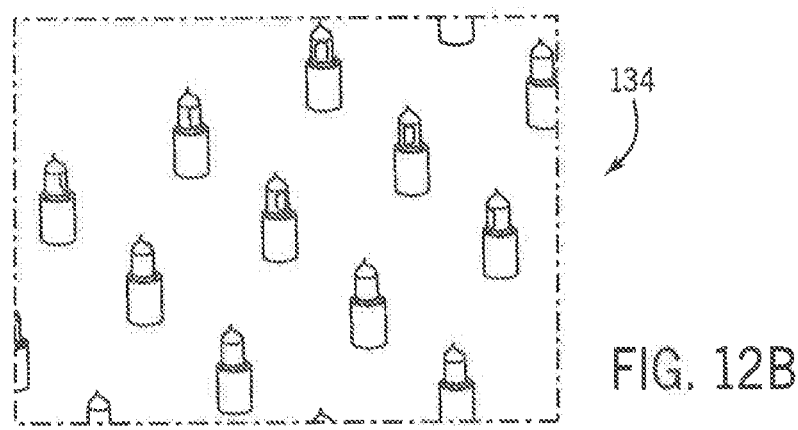
Figure 12C:
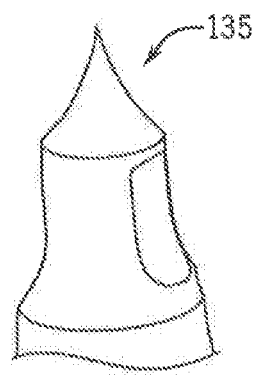
Figure 12D:
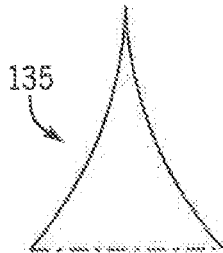

Referring to FIGS. 10A and 10B, a microneedle array 134, also available from Debiotech, can replace the patch 124 or cannula. This microneedle array 134 is proposed here as an option because it is an excellent match for the Nanopump™ pump, although it may be used in combination with any TMJ micropump. Microneedles 135 are less invasive, cause little or no pain to the patient and minimize the risk of infections. FIGS. 10A, 10B, 11 and 12A-D show the microneedle array with details. FIG. 10B shows the size of the microneedle array in reference to a typical wooden match 133.

In some embodiments, the microneedle array 134 may be the NanoJect™ microneedle array is based on a biocompatible MEMS technology. The technology has the following features: extremely sharp needles that are robust and skin friendly; protected side holes to avoid coring during penetration; controlled length for painless penetration and low dead volume; and MEMS fabrication for biocompatibility, mass production and precision.

The NanoJect™ microneedle array has been designed to overcome the challenges of conventional intradermal delivery techniques, while improving accurate site and dose delivery. The microneedle array 134 is made of hollow microneedles with a unique side protected delivery hole. By placing the hole on the side of the needle at a precise depth, the skin can be punctured without coring and without removing any tissue. Because the skin remains intact above the side hole, leakage during injection is prevented and healing is improved. Furthermore, by injecting through the side hole, where the needle does not apply direct pressure on the tissue, liquid can diffuse more easily at a better defined and controlled depth. This enables pain free injections of up to 0.5 milliliters in only 5 seconds.

The NanoJect™ microneedle array comprises microneedles produced with MEMS (Micro-Electro Mechanical Systems) technology. By exactly controlling the position and orientation of the side hole on each microneedle, it is possible to target a precise intradermal site and control drug or vaccine distribution. At the same time, the tip of the microneedle can be made extremely sharp and without any protrusion to perfectly enter the skin at a 90° angle. The MEMS technology used to manufacture the microneedles make them very strong and provides them with excellent biocompatibility properties.

NanoJect™ microneedle array is available in multiple possible configurations: single or multiple silicon microneedles with a length ranging from 350 to 900 microns, having one or multiple hollow bores connected to a syringe. While every microneedle is smaller than a 33G needle, the dimension of the bore is well adapted for delivery of larger particles and long peptides. Human in vivo injections of 100 microliters in less than 2 seconds and up to 500 microliters in less than 5 seconds have been performed in a controlled and reproducible way. These were done without specific preliminary training of the personnel. A microneedle array 134 offers several advantages: improved usability, reproducibility, reliability, accuracy of dose administration with barely any pain, as well as reduction in risk of needle stick injuries for healthcare workers.

Figure 13:
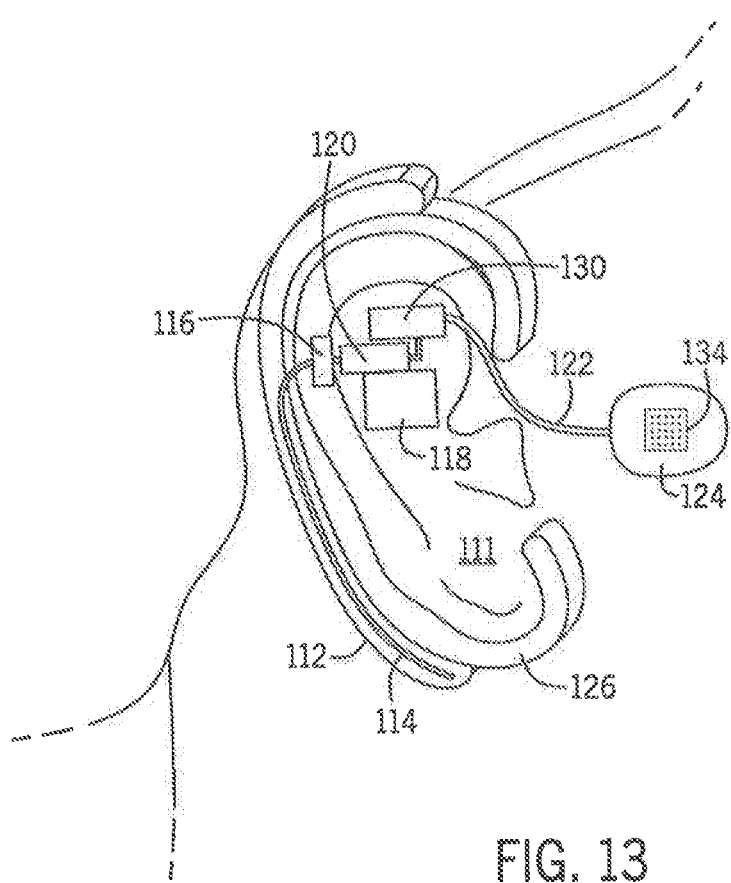
FIG. 13 is a schematic rendition of another TMJ prototype infusion system according to the disclosure worn by a human subject.

As an option for the TMJ infusion system, it is proposed to use a microneedle array 134 for drug injection instead of a cannula. It is proposed to integrate a microneedle array 134 into the patch 124, which may be a diabetic patch, for attachment to the subject's skin. This embodiment of the infusion system is schematically shown in FIG. 13. The microneedle array 134 is shown in its approximate and proportional size.

This embodiment of the infusion system shown in FIG. 13 is based on components available from manufacturers and vendors. Table 2 is a compilation of components suitable for use in this embodiment of the infusion system. It is to be appreciated that these components are non-limiting examples of components that could be used in this system. At least one example of components that could be used instead of those listed in the table are the micropumps disclosed in FIGS. 5 and 6, which may be implemented in any of the embodiments discussed herein

TABLE 2

List of components

| Item | Description | Source |
| --- | --- | --- |
| Pump(s) Qty.: 1 | Piezoelectric micropump Model: Nanopump ™ | Debiotech S.A., Lausanne, Switzerland |
| Injector Qty.: 1 | Microneedle array Model: Nanoject ™ | Debiotech S.A., Lausanne, Switzerland |
| Ear hook | Earhook looping entirely around auricle for excellent hold. Model: 56518 | Mfg.: Motorola |

Figure 14A:
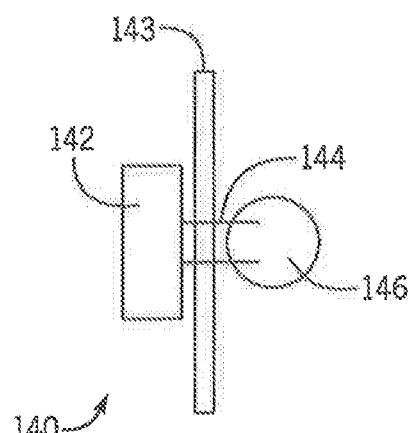
FIGS. 14A and 14B show schematic renditions of a TMJ infusion system according to the disclosure worn by a human subject.
Figure 14B:
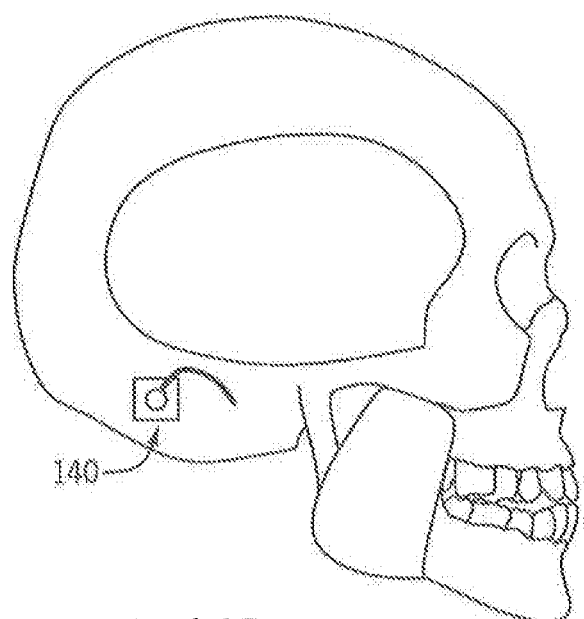

FIGS. 14A and 14B show another embodiment of an infusion system 140 which can feature a pump 142 embedded in temporal area 143 (for example in a subcutaneous position) with a microneedle system 144 to periodically deliver fluid to the subject and a patch 146. Some non-limiting examples of fluid to be delivered include muscle relaxant agents for TMJ-pain/discomfort.

Figure 15:
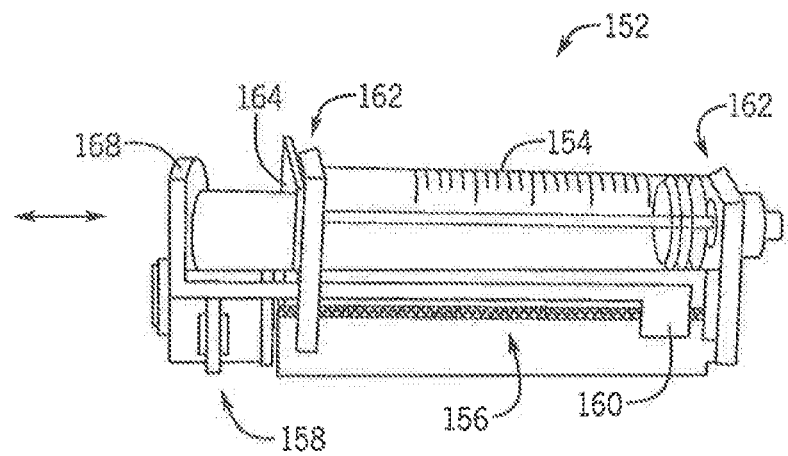
FIG. 15 is a custom-built 5 milliliter syringe pump suitable for use in an infusion system according to the disclosure.
Figure 16:
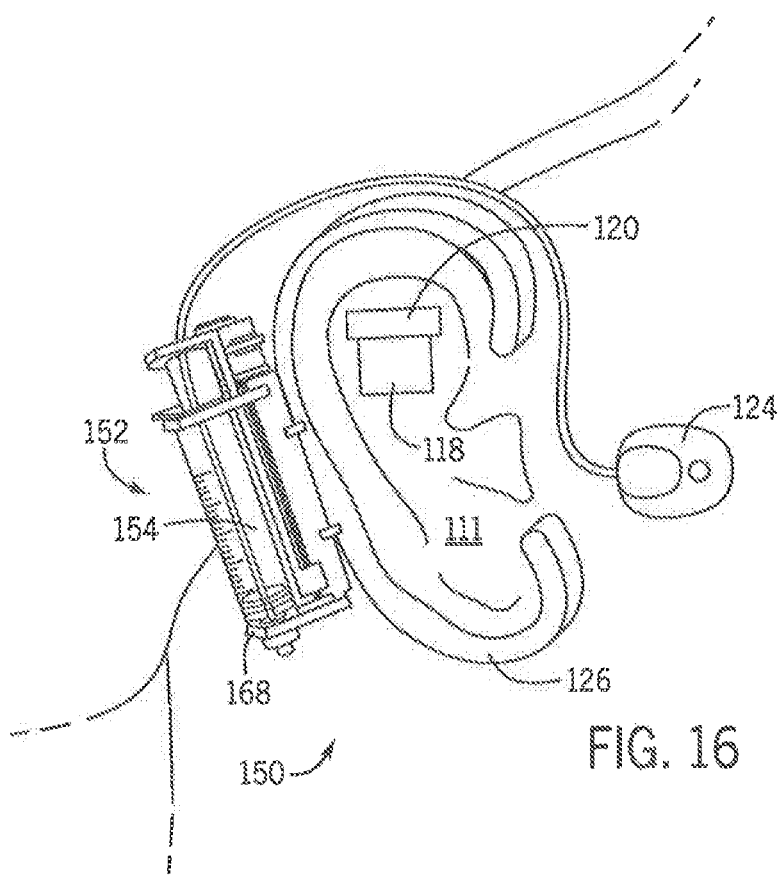
FIG. 16 is a schematic rendition of another TMJ prototype infusion system according to the disclosure worn by a human subject.
Figure 17:
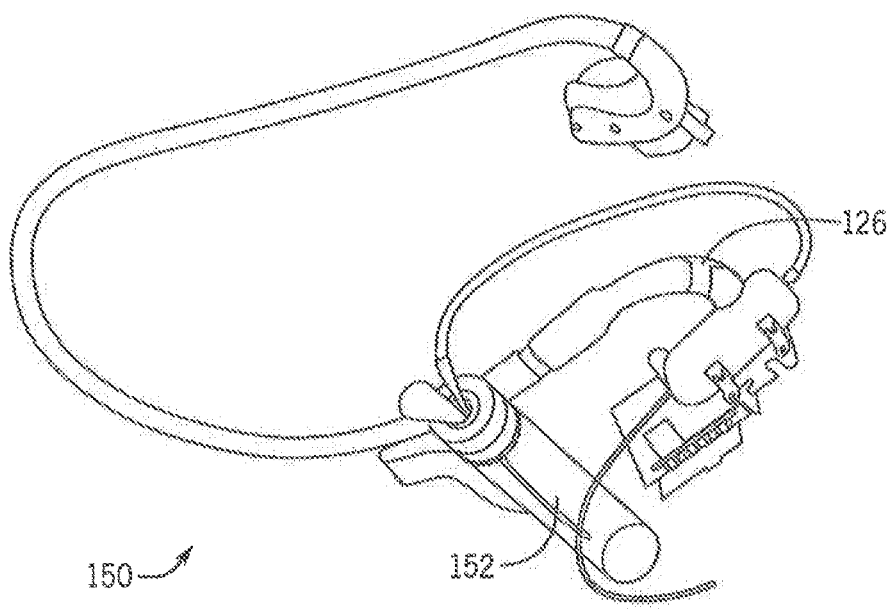
FIG. 17 is a photograph of another TMJ prototype infusion system according to the disclosure. This infusion system includes an alternative support frame attached to the source of the fluid and the fluid delivery system. The support frame can wrap around the back of a human's head. It has the advantage that system components can be distributed between the left and right side to increase wear comfort and balance the weight.

FIGS. 15, 16, 17 show yet another non-limiting example embodiment of the infusion system 150 that was developed for use in treating temporomandibular joint (TMJ) pain. The previously described concepts propose micropumps both of which rely on piezoelectric actuation and require voltages of 100V or more. In this configuration, a syringe pump 152 is proposed of which a reservoir 154 is an integral part. For example, if the syringe pump 152 uses a disposable syringe as reservoir then sterility can easily be assured and no special drug reservoir is required. In this configuration, a custom-built syringe pump 152 is shown that accommodates a standard 5 ml disposable syringe with Luer-Lok™ tip. Syringe pumps have the advantage that the syringe itself is the reservoir for the drug and may be configured as a sterile and disposable drug container, thus serving a dual purpose.

In the example application of the infusion system 110 for TMJ, the drug reservoir is a component comprising a substantial fraction of the volume of the entire system. A custom-built syringe pump with a compact design around a specific syringe format adds only a small volume and little weight to the infusion system 150. The syringe pump 152 does not rely on valves and is impervious to back flow. It is a positive displacement pump, making metering easy and precise. The pressure it can produce is practically limited by the torque of the drive motor. In a non-limiting embodiment the drive motor can be of the stepper motor kind. The operating voltage of a stepper motor can be as low as 3V. Dosing is inherently precise because the number of steps taken by the motor are directly proportional to the injected fluid volume.

This custom-designed syringe pump 152 is shown in FIG. 15. The syringe pump 152 is based on a linear screw 156 with micro stepper motor 158 actuation. The frame 160 of the screw-stepper motor assembly serves a dual purpose as frame for the syringe pump 152. Quick-release clasps 162 attached to the frame hold the 5 ml syringe firmly in place. The syringe plunger 164 is advanced by a draw bar 168 that is moved by the linear screw 156. The linear screw 156 can have a length at or around 33 millimeters and the motor can have a diameter of 8 millimeters in some non-limiting embodiments. The infusion system 150 with the syringe pump 152 worn by a subject is schematically shown in FIG. 16.

This embodiment of the infusion system 150 shown in FIG. 16 is based on components available from manufacturers and vendors. The syringe pump may require some custom fabrication. Table 3 is a compilation of these components needed for all steps presented in this embodiment development. It is to be appreciated that these components are non-limiting examples of components that could be used in this system.

TABLE 3

List of components

| Item | Description | Source |
|---|---|---|
| Pump Actuator Qty.: 1 | Linear screw actuator with stepper motor Model: micro stepper motor for camera lens focusing/ Item No.: 151007686281 | Worldwindow2010 Shenzhen City, China |
| Syringe (reservoir) Qty.: 1 | Disposable general purpose syringe Model: Becton-Dickinson 5 ml, precision-glide. Luer-Lok ™ tip. Mfg. No.: 309646 | Distributor.: MG Scientific Pleasant Prairie, WI |
| Ear hook | Earhook looping entirely around auricle for excellent hold. Model: 56518 | Mfg.: Motorola |

The embodiments described above may be used in a number of applications. Some non-limiting examples of areas of dental applications for the micro-fluid infusion systems described herein include: temporo-mandibular joint disorder, trigeminal neuralgia, post-operative pain, target agents, analgesic, local-anesthetic, vasoconstrictor, neuro-muscular relaxant, antibiotic, drug-cocktail, among others.

Furthermore, many options exist for the drug delivery conduit. Non-limiting examples are: implanted indwelling cannula with plug that can include fluid introduced by practitioner during office visit; implanted passive membrane-based reservoir, deployed external muscle contraction (e.g., of masseter muscle), through external electrical stimulation; implant in-dwelling cannula and reservoir system mimicking the placement of a salivary gland (e.g. parotid gland); infusion tubing system which is semi-permeable, or has micro-holes for diffuse irrigation of chemical such as in a "soaker hose"; pump embedded in temporal area (for example in a subcutaneous position) with a microneedle system to periodically deliver muscle relaxant agents for TMJ-pain/discomfort.

Thus, the disclosure provides an infusion system for subcutaneous delivery of a fluid to a subject.

Although the disclosure has been described in considerable detail with reference to certain embodiments, one skilled in the art will appreciate that the present disclosure can be practiced by other than the described embodiments, which have been presented for purposes of illustration and not of limitation. Therefore, the scope of the appended claims should not be limited to the description of the embodiments contained herein.

What is claimed is:

1. An infusion system for subcutaneous delivery of a fluid to a subject, the infusion system comprising:
   a source of a fluid;
   a fluid delivery system;
   a first fluid conduit in fluid communication with the source of the fluid and the fluid delivery system;
   a fluid injection device configured to be inserted into the skin of a subject for delivering the fluid to the subject;
   a second fluid conduit in fluid communication with the fluid delivery system and the fluid injection device; and
   a support frame attached to the source of the fluid and the fluid delivery system, the support frame being configured to loop around a body part of the subject to mount the source of the fluid and the fluid delivery system on a region of a head of the subject,
   wherein the fluid delivery system moves the fluid from the source of the fluid, through the first fluid conduit, through the second fluid conduit, and through the fluid injection device,
   wherein the fluid injection device comprises an adhesive patch for securing the fluid injection device to the skin of the subject, and
   wherein the adhesive patch is located at a distal end of the second fluid conduit.

2. The infusion system of claim 1 wherein:
   the fluid delivery system is configured such that the fluid injection device delivers 10 to 100 microliters per minute of the fluid to the subject.

3. The infusion system of claim 1 wherein:
   the fluid delivery system includes a pump in fluid communication with the first fluid conduit and the second fluid conduit, the pump moving the fluid from the source of the fluid, through the first fluid conduit, through the second fluid conduit, and through the fluid injection device.

4. The infusion system of claim 3 wherein:
   the pump is a piezoelectrically actuated pump.

5. The infusion system of claim 3 wherein:
the pump is a membrane pump.
6. The infusion system of claim 3 wherein:
the pump is a vane pump.
7. The infusion system of claim 3 wherein:
the pump is a scroll pump.
8. The infusion system of claim 3 wherein:
the pump is a screw pump.
9. The infusion system of claim 3 wherein:
the pump is a progressing cavity pump.
10. The infusion system of claim 3 wherein:
the pump is a gear pump.
11. The infusion system of claim 3 wherein:
the pump is a peristaltic pump.
12. The infusion system of claim 3 wherein:
the pump produces a pressure of 10 kPa or greater.
13. The infusion system of claim 3 wherein:
the pump produces a pressure of 100 kPa or greater.
14. The infusion system of claim 3 wherein:
the fluid delivery system includes a check valve that prevents backflow into the pump.
15. The infusion system of claim 3 wherein:
the fluid delivery system includes a battery power supply in electrical communication with a controller,
the controller is in electrical communication with the battery power supply and the pump, and
the controller is configured to actuate the pump to move the fluid from the source of the fluid, through the first fluid conduit, through the second fluid conduit, and through the fluid injection device.
16. The infusion system of claim 15 wherein:
the controller has a wired communication port to at least one of a computer, a smart phone, and an appropriate controller module, running software applications with graphical user interfaces for control, monitoring and data logging.
17. The infusion system of claim 15 wherein:
the controller has wireless communication using a secure wireless communication protocol to at least one of a computer, a smart phone, and an appropriate controller module, running software applications with graphical user interfaces for control, monitoring and data logging.
18. The infusion system of claim 3 wherein:
the pump comprises one or more double acting piezo actuators.
19. The infusion system of claim 3 wherein:
the pump is valve-less.
20. The infusion system of claim 1 wherein:
the fluid injection device comprises: a cannula configured to be inserted into the skin of the subject for delivering the fluid to the subject, and the adhesive patch is configured for securing the cannula to the skin of the subject, and
the adhesive patch is wider than the second fluid conduit.
21. The infusion system of claim 1 wherein:
the fluid injection device comprises: a microneedle array including microneedles configured to be inserted into the skin of the subject for delivering the fluid to the subject, and the adhesive patch is configured for securing the microneedle array to the skin of the subject, and
the adhesive patch is wider than the second fluid conduit.
22. The infusion system of claim 1 wherein:
the support frame is structured to loop around at least a portion of an ear of the subject.
23. The infusion system of claim 1 wherein:
the support frame is structured to loop around a neck of the subject.
24. The infusion system of claim 1 wherein:
the support frame is structured to loop around the top of the head of the subject.
25. The infusion system of claim 1 wherein:
the support frame is structured to loop around at least one of a top of the head and a neck and a forehead of the head of the subject.
26. The infusion system of claim 1 wherein:
the fluid comprises a pain medication.
27. The infusion system of claim 1 wherein:
the fluid comprises a medication for treating temporomandibular joint pain.
28. A method for treating temporomandibular joint dysfunction in a subject, the method comprising:
(a) providing an infusion system, the infusion system comprising: a source of a fluid, a fluid delivery system, a first fluid conduit in fluid communication with the source of the fluid and the fluid delivery system, a fluid injection device configured to be inserted into a skin of the subject for delivering the fluid to the subject, a second fluid conduit in fluid communication with the fluid delivery system and the fluid injection device, and a support frame attached to the source of the fluid and the fluid delivery system, the support frame being configured to loop around a body part of the subject to mount the source of the fluid and the fluid delivery system on a region of a head of the subject, wherein the fluid delivery system moves the fluid from the source of the fluid, through the first fluid conduit, through the second fluid conduit, and through the fluid injection device;
(b) inserting the fluid injection device of the infusion system into a skin of the subject for delivering the fluid to the subject; and
(c) activating the fluid delivery system to move the fluid from the source of the fluid, through the first fluid conduit, through the second fluid conduit, and through the fluid injection device,
wherein the fluid comprises a medication for treating temporomandibular joint pain,
wherein the fluid injection device comprises an adhesive patch for securing the fluid injection device to the skin of the subject, and
wherein the adhesive patch is located at a distal end of the second fluid conduit.

* * * * *